US012605414B2

(12) United States Patent
Kweon et al.

(10) Patent No.: US 12,605,414 B2
(45) Date of Patent: Apr. 21, 2026

(54) **DISCOVERY OF NOVEL *AKKERMANSIA MUCINIPHILA* AK32 AND APPLICATION THEREOF FOR IMPROVING INTESTINAL FUNCTION**

(71) Applicants:THE ASAN FOUNDATION, Seoul (KR); UNIVERSITY OF ULSAN FOUNDATION FOR INDUSTRY COOPERATION, Ulsan (KR)

(72) Inventors: Mi-Na Kweon, Seoul (KR); Seungil Kim, Ansan-si (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 583 days.

(21) Appl. No.: 17/998,537

(22) PCT Filed: May 7, 2021

(86) PCT No.: PCT/KR2021/005747
§ 371 (c)(1),
(2) Date: Nov. 11, 2022

(87) PCT Pub. No.: WO2021/230581
PCT Pub. Date: Nov. 18, 2021

(65) Prior Publication Data
US 2023/0321160 A1 Oct. 12, 2023

(30) Foreign Application Priority Data
May 11, 2020 (KR) ........................ 10-2020-0056034

(51) Int. Cl.
*A61K 35/741* (2015.01)
*A61K 35/38* (2015.01)
(Continued)

(52) U.S. Cl.
CPC ............ *A61K 35/741* (2013.01); *A61K 35/38* (2013.01); *A61P 1/04* (2018.01); *C12N 1/205* (2021.05); *C12R 2001/01* (2021.05)

(58) Field of Classification Search
CPC ......... A61K 35/741; A61K 35/74; A61P 1/04; A61P 1/00; C12N 1/205; C12N 1/20; C12R 2001/01; A23L 33/135
See application file for complete search history.

(56) References Cited

U.S. PATENT DOCUMENTS 10,537,597 B2   1/2020   O'Mahony et al.
10,736,924 B2   8/2020   Cani et al.
(Continued)

FOREIGN PATENT DOCUMENTS

KR   10-2017-0103140 A   9/2017
KR   10-2018-0053336 A   5/2018

OTHER PUBLICATIONS

Bian et al., Administration of Akkermansia muciniphila Ameliorates Dextran Sulfate Sodium-Induced Ulcerative Colitis in Mice. Front Microbiol. Oct. 1, 2019;10:2259 (Year: 2019).*
Zhai et al.,Strain-Specific Anti-inflammatory Properties of Two Akkermansia muciniphila Strains on Chronic Colitis in Mice, Front. Cell. Infect. Microbiol., vol. 9—2019 (Year: 2019).*
Zhu et al., Akkermansia muciniphila protects intestinal mucosa from damage caused by S. pullorum by initiating proliferation of intestinal epithelium. Vet Res 51, 34 (2020) (Year: 2020).*
(Continued)

*Primary Examiner* — Robert B Mondesi
*Assistant Examiner* — Naghmeh Nina Moazzami
(74) *Attorney, Agent, or Firm* — Oblon, McClelland, Maier & Neustadt, L.L.P.

(57) ABSTRACT

An *Akkermansia muciniphila* AK32 (Accession No. KCTC 14172BP) strain. The *Akkermansia muciniphila* AK32 strain prevents or improves intestinal damage. A method for preventing, improving or treating intestinal damage, including administering to a subject an effective amount of the *Akkermansia muciniphila* AK32 strain or a culture thereof as an active ingredient.

3 Claims, 11 Drawing Sheets
Specification includes a Sequence Listing.

A. muciniphila
AK32

(51) Int. Cl.

| | |
|---|---|
| *A61P 1/04* | (2006.01) |
| *C12N 1/20* | (2006.01) |
| *C12N 1/205* | (2026.01) |
| *C12R 1/01* | (2006.01) |

(56) References Cited

U.S. PATENT DOCUMENTS

| | | |
|---|---|---|
| 10,960,032 B2 | 3/2021 | O'Mahony et al. |
| 2018/0250347 A1 | 9/2018 | Cani et al. |
| 2018/0296613 A1 | 10/2018 | O'Mahony et al. |
| 2020/0164003 A1 | 5/2020 | O'Mahony et al. |
| 2021/0015876 A1 | 1/2021 | Cani et al. |

OTHER PUBLICATIONS

International Search Report mailed on Aug. 23, 2021 in PCT/KR2021/005747 filed on May 7, 2021, 5 pages.

Reunanen et al., "*Akkermansia muciniphila* Adheres to Enterocytes and Strengthens the Integrity of the Epithelial Cell Layer", Applied and Environmental Microbiology, vol. 81, No. 11, 2015, pp. 3655-3662, 9 total pages.

Macchione et al., "*Akkermansia muciniphila*: key player in metabolic and gastrointestinal disorders", European Review for Medical and Pharmacological Sciences, vol. 23, 2019, pp. 8075-8083, 10 total pages.

* cited by examiner

FIG. 2

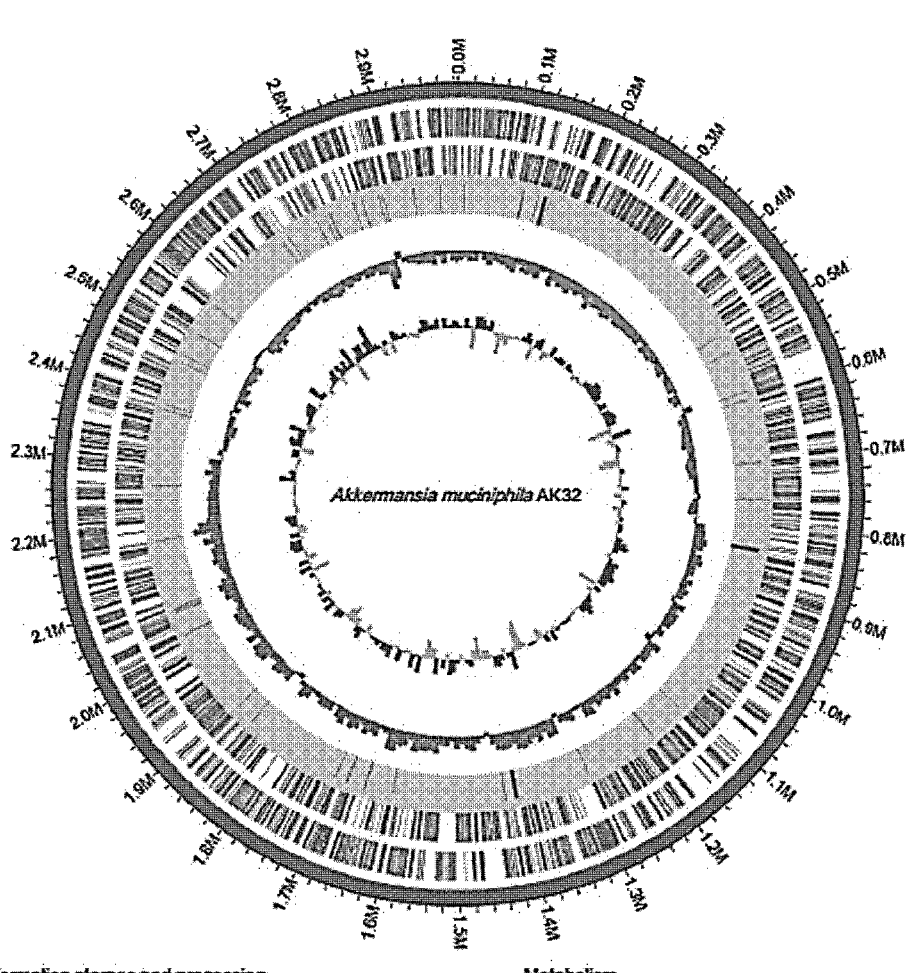

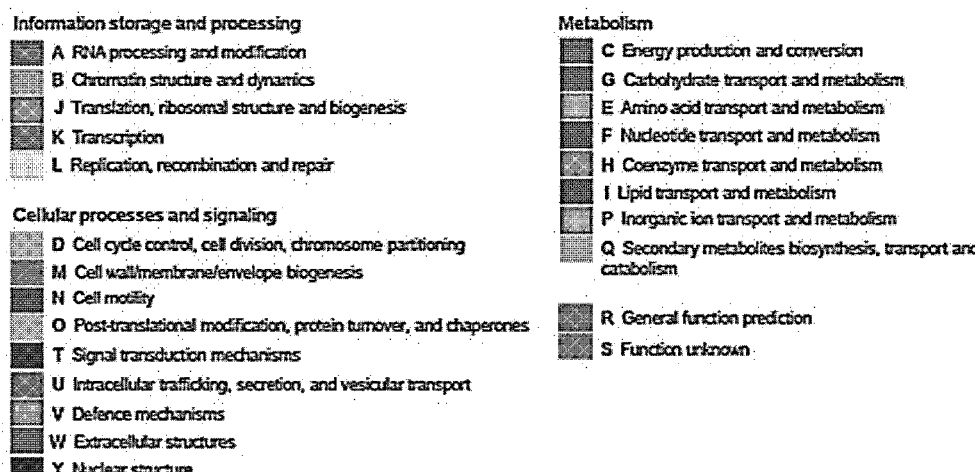

Information storage and processing

- A RNA processing and modification
- B Chromatin structure and dynamics
- J Translation, ribosomal structure and biogenesis
- K Transcription
- L Replication, recombination and repair

Cellular processes and signaling

- D Cell cycle control, cell division, chromosome partitioning
- M Cell wall/membrane/envelope biogenesis
- N Cell motility
- O Post-translational modification, protein turnover, and chaperones
- T Signal transduction mechanisms
- U Intracellular trafficking, secretion, and vesicular transport
- V Defence mechanisms
- W Extracellular structures
- Y Nuclear structure
- Z Cytoskeleton

Metabolism

- C Energy production and conversion
- G Carbohydrate transport and metabolism
- E Amino acid transport and metabolism
- F Nucleotide transport and metabolism
- H Coenzyme transport and metabolism
- I Lipid transport and metabolism
- P Inorganic ion transport and metabolism
- Q Secondary metabolites biosynthesis, transport and catabolism

- R General function prediction
- S Function unknown

FIG. 3A

```
BAA-835  MLLARAFDTKISSLYKAGKITGGVYLGRGHEAIAACGGVFLTAGYDVIAPFIREQAARVT
AK32     MLLARAFDTKISSLYKAGKITGGVYLGRGHEAIAACGGVFLTAGYDVIAPFIREQAARVT
         ************************************************************

BAA-835  WGEPIIEAARAYLGSALGYMKGRDGNVHRGLPAEGYMAPISHLGSTVAFVIGCLFAKRLD
AK32     WGEPIIEAARAYLGSALGYMKGRDGNVHRGLPAEGYMAPISHLGSTVAFVIGCLFAKRLD
         ************************************************************

BAA-835  GKLPGPVGVAFCGDGTTSTGAFHEAANMANVERLPLVLVVTNNQFAYSTPNIREFGEASL
AK32     GKLPGPVGVAFCGDGTTSTGAFHEAANMANVERLPLVLVVTNNQFAYSTPNIREFGEASL
         ************************************************************

BAA-835  ADRGRGYGFTVHETDGTDFMATLETFRTAVNNAREGRGPQWVLAKTLRMCGHGEHDDASY
AK32     ADRGRGYGFTVHETDGTDFMATLETFRTAVNNAREGRGPQWVLAKTLRMCGHGEHDDASY
         ************************************************************

BAA-835  IPRELKEEYEKKDPVAVAERQLLAAGWLTPEETAALKKQYADEVQLAVATAQREPEPDPF
AK32     IPRELKEEYEKKDPVAVAERQLLAAGWLTPEETAALKKQYADEVQLAVATAQREPEPDPF
         ************************************************************

BAA-835  REDWNATVWRPY
AK32     REDWNATVWRPY
         ************
```

FIG. 3B

```
BAA-835   MSLFDSLITFLQGMGVFSLSWQMVGMWGIAILLLYLGVAKQYEPLLMVPIAFGALIANIP
AK32      MSLFDSLITFLQGMGVFSLSWQMVGMWGIAILLLYLGVAKQYEPLLMVPIAFGALIANIP
          ************************************************************

BAA-835   DNGMLITQLNQQVISSNEQGEVTATSLNNVGYLRVHVAPLQQAPSKVPANLTTPESRAQY
AK32      DNGMLITQLNQQVISSNEQGEVTSTSLNNVGYLRVHVAPLQQTPARVPANLTTPEARAQY
          ***********************.:*************** .*:.**********:.****

BAA-835   QEIMQQPMQVYPGSQLTVSKIKSVRESQEKAKADAARLGDDSLTVDPNLKDFQNVTEDNG
AK32      LETMQQPMQVYPGSQLTVSKIKSVRESQEKAKADAARLGDDSLTVDPNLKDFQNVTEDNG
          *  *********************************************************

BAA-835   NEPVFLLTNGEGTTVVRQQGVNYFDTSGNRIPVDLKTQKLEPLVVSAAGKYVAVGQHTQE
AK32      NEPVFLLTNGEGTTVVRQQGVNYFDTSGNRVPVDLKTQKLEPLVVSAAGKYVAVGQHTQE
          *****************************.:*****************************

BAA-835   LLVTSIHGGLYDWIGLGIKAEIFPPIIFLGVGALTDFGPLLAAPRTLLLGAAAQVGVAAT
AK32      LLVTSIHGGLYDWIGLGIKAEIFPPIIFLGVGALTDFGPLLAAPRTLLLGAAAQVGVAAT
          ************************************************************

BAA-835   FFMALFMGFTPNESASIGIIGGADGPTSIFLTMKLAPHLLGAVAVAAYTYMSLVPLIQPP
AK32      FFMALFMGFNPNEAASIGIIGGADGPTSIFLTMKLAPHLLGAVAVAAYTYMSLVPLIQPP
          *********.***:.*********************************************

BAA-835   IMALLTTKKERLIRMKSLRTVSKSEKLFFAVLVTIVTILLIPDASPLIGMLMLGNFLREC
AK32      IMALLTTKKERLIRMKSLRTVSKSEKLFFAVLVTIVTILLIPDASPLIGMLMLGNFLREC
          ************************************************************

BAA-835   KVTERLVQASQNEIINIVTIFLGTSVGLTMQGDRFLQSETLLIILLGIVAFGVATAGGVI
AK32      KVTERLVQASQNEIINIVTIFLGTSVGLTMQGDRFLQAETLLIILLGIVAFGVATAGGVI
          *************************************.:*********************

BAA-835   AAKIMNLIWRKNPVNPLIGSAGVSAVPMAARVSHNVGQKYDPSNYLLMHAMGPNVAGVIG
AK32      AAKLMNLIWRKNPVNPLIGSAGVSAVPMAARVSHNVGQKYDPSNYLLMHAMGPNVAGVIG
          ***.*******************************************************

BAA-835   TAVIAGYYIATLAK
AK32      TAVIAGYYIATLAK
          **************
```

FIG.4B
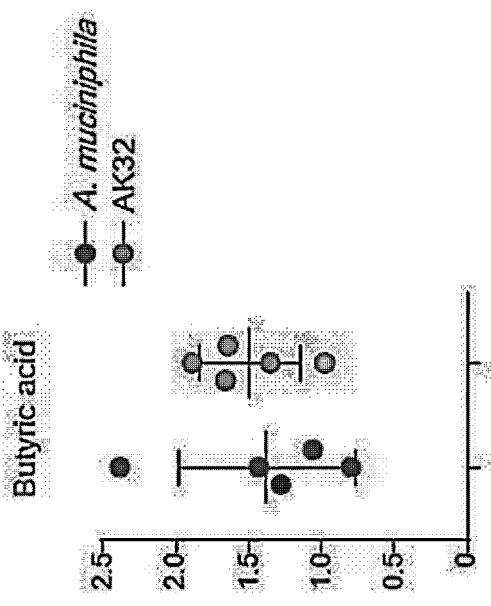
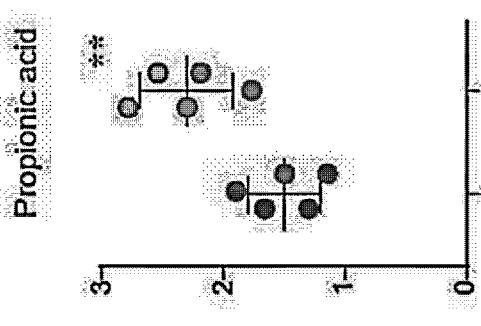
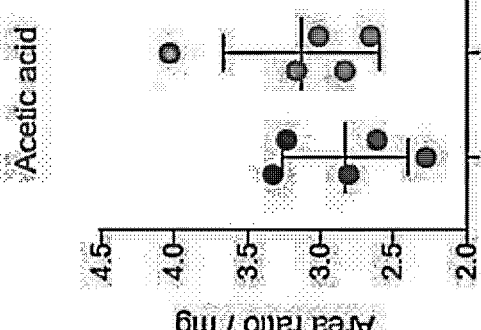

DISCOVERY OF NOVEL *AKKERMANSIA MUCINIPHILA* AK32 AND APPLICATION THEREOF FOR IMPROVING INTESTINAL FUNCTION

CROSS REFERENCE TO RELATED APPLICATIONS

This application is a National Stage entry under 35 U.S.C. § 371 of PCT/KR2021/005747, filed on May 7, 2021, and claims priority to Korean Patent Application No. 10-2020-0056034, filed on May 11, 2020. The entire contents of both are incorporated herein by reference.

TECHNICAL FIELD

The present invention relates to a novel strain of *Akkermansia muciniphila* AK32 and a composition for preventing or treating intestinal injury, which includes the same.

This application claims priority to and the benefit of Korean Patent Application No. 10-2020-0056034, filed on May 11, 2020, the disclosure of which is incorporated herein by reference in its entirety.

BACKGROUND ART

An inflammatory bowel disease is an idiopathic disease that causes chronic and recurrent inflammation of the digestive organs and damage to intestinal mucosa tissue.

In general, Crohn's disease (CD) and ulcerative colitis (UC) are called inflammatory bowel diseases, and although the cause is not clearly known, it is suggested that the disease is caused by genetic findings, immune and environmental factors, and some microorganisms (pathogens).

More specifically, an increase in inflammatory cytokines caused by immune dysfunction of the intestinal wall or the invasion of environmental antigens in the intestine and dysbiosis of intestinal microbiota caused by pathogenic infection, are suggested as major causes. Particularly, it is known that the diversity of intestinal bacteria is reduced, and dysbiosis is caused by the excessive proliferation and adhesion of Enterobacteriaceae among specific symbiotic bacteria Proteobacteria, and infection by specific pathogens such as invasive *E. coli* (AIEC) and *Mycobacterium*.

Meanwhile, as the antibacterial effect and the effect of alleviating an inflammatory disease through immunoregulation in the body of lactic acid bacteria are confirmed, studies have been conducted to prevent colitis or improve symptoms of colitis using lactic acid bacteria.

Particularly, probiotic lactic acid bacteria prevent pathogenic bacteria from adhering to the intestine, and prevent the invasion of pathogenic bacteria by producing their own antibacterial materials such as lactic acid and bacteriocin. The regulation of intestinal microbiota in which dysbiosis occurs due to such pathogenic microorganisms may affect a specific organ of a host and may affect the interaction between intestinal microbiota and the intestinal mucosa. In addition, the function of the intestinal mucosa may be improved by increasing the adhesion to the intestinal mucosa and mucus secretion, the production of a protective material such as mucin, and the tight junction integrity of the intestinal mucosa.

*Lactobacillus* sp., *Bifidobacterium* sp., *Saccharomyces boulardii*, *Escherichia coli* Nissle1917, and the multi-lactobacillus product VSL#3 are most commonly used in treatment of an inflammatory bowel disease. Particularly, the effect of probiotics on an inflammatory bowel disease was most excellently exhibited in the treatment of pouchitis in ulcerative colitis patients after surgery.

However, despite the potential effects of these probiotic microorganisms, the mechanism of action of probiotics has not yet been clearly elucidated, and additional research results are required accordingly.

DISCLOSURE

Technical Problem

The technical problem to be achieved by the present invention is to provide an *Akkermansia muciniphila* (*A. muciniphila*) AK32 (Accession No. KCTC 14172BP) strain, and the present inventors confirmed that the novel AK32 strain of the present invention not only increases the crypt height and the number of goblet cells in the small intestine, but also promotes the expression of genes related to the proliferation and differentiation of epithelial cells in the small intestine and is effective in the regeneration and growth of small intestine tissue.

Therefore, the present invention is directed to providing the *A. muciniphila* AK32 (Accession No. KCTC 14172BP) strain.

The present invention is also directed to providing a pharmaceutical composition for preventing or treating intestinal damage, which includes the *A. muciniphila* AK32 stain or a culture thereof as an active ingredient.

The present invention is also directed to providing a food composition for preventing or improving intestinal damage, which includes the *A. muciniphila* AK32 stain or a culture thereof as an active ingredient.

The present invention is also directed to providing a food composition for improving intestinal function, which includes the *A. muciniphila* AK32 stain or a culture thereof as an active ingredient.

The present invention is also directed to providing a probiotic, which includes the *A. muciniphila* AK32 strain or a culture thereof as an active ingredient.

The present invention is also directed to providing a composition for an intestinal drug, which includes the *A. muciniphila* AK32 strain or a culture thereof as an active ingredient.

The present invention is also directed to providing a probiotic product composition, which includes the *A. muciniphila* AK32 strain or a culture thereof as an active ingredient.

The present invention is also directed to providing a food additive composition, which includes the *A. muciniphila* AK32 strain or a culture thereof as an active ingredient.

However, technical problems to be solved in the present invention are not limited to the above-described problems, and other problems which are not described herein will be fully understood by those of ordinary skill in the art from the following descriptions.

Technical Solution

To solve the above problems, the present invention provides an *A. muciniphila* AK32 (Accession No. KCTC 14172BP) strain.

The present invention also provides a pharmaceutical composition for preventing or treating intestinal damage, which includes the *A. muciniphila* AK32 stain or a culture thereof as an active ingredient.

The present invention also provides a food composition for preventing or improving intestinal damage, which includes the *A. muciniphila* AK32 stain or a culture thereof as an active ingredient.

The present invention also provides a food composition for improving intestinal function, which includes the *A. muciniphila* AK32 stain or a culture thereof as an active ingredient.

The present invention also provides a probiotic, which includes the *A. muciniphila* AK32 strain or a culture thereof as an active ingredient.

The present invention also provides a composition for an intestinal drug, which includes the *A. muciniphila* AK32 strain or a culture thereof as an active ingredient.

The present invention also provides a probiotic product composition, which includes the *A. muciniphila* AK32 strain or a culture thereof as an active ingredient The present invention also provides a food additive composition, which includes the *A. muciniphila* AK32 strain or a culture thereof as an active ingredient.

In one embodiment of the present invention, the *A. muciniphila* AK32 may prevent or improve intestinal damage, but the present invention is not limited thereto.

In another embodiment of the present invention, the *A. muciniphila* AK32 may produce a methylmalonylCoA/oxaloacetate decarboxylase beta subunit (MMD) enzyme including an amino acid sequence of SEQ ID NO: 3, but the present invention is not limited thereto.

In still another embodiment of the present invention, the *A. muciniphila* AK32 may promote the proliferation of intestinal epithelial cells, but the present invention is not limited thereto.

In yet another embodiment of the present invention, the intestinal damage may be one or more selected from the group consisting of radiation-induced intestinal damage, drug-induced intestinal damage, alcohol-induced intestinal damage, and intestinal damage caused by an inflammatory bowel disease, but the present invention is not limited thereto.

In yet another embodiment of the present invention, the inflammatory bowel disease may be one or more selected from the group consisting of a duodenal ulcer, an intestinal obstruction, acute gastrointestinal bleeding, Crohn's disease, enteric Behcet's disease, pouchitis, irritable bowel syndrome, and ulcerative colitis, but the present invention is not limited thereto.

In addition, the present invention provides a method of preventing, improving or treating intestinal damage, which includes administering the composition including the *A. muciniphila* AK32 strain or a culture thereof into a subject.

In addition, the present invention provides a use of the composition including the *A. muciniphila* AK32 strain or a culture thereof for prevention, improvement, or treatment of intestinal damage.

In addition, the present invention provides a use of the composition including the *A. muciniphila* AK32 strain or a culture thereof to produce a drug used for intestinal damage.

Advantageous Effects

The *Akkermansia muciniphila* AK32 (Accession No. KCTC 14172BP) strain of the present invention not only increases the crypt height and the number of goblet cells in the small intestine, but also promotes the expression of genes related to the proliferation of intestinal epithelial cells and is effective in regeneration and growth of intestinal tissue and small intestinal organoids, so it is effective in preparation of foods, pharmaceuticals, intestinal drugs, probiotic products, and probiotics.

DESCRIPTION OF DRAWINGS

FIG. 2 is the complete genome map of the AK32 strain.

FIG. 3A shows the comparison in PDH amino acid sequence between the AK32 strain and the BAA-835 strain.

FIG. 3B shows the comparison in MMD amino acid sequence between the AK32 strain and the BAA-835 strain.

FIG. 4B shows the result of comparing SCFA in the cecal contents after oral administration of each of the AK32 strain and the BAA-835 strain to mice for 4 weeks.

MODES OF THE INVENTION

Figure 1A:
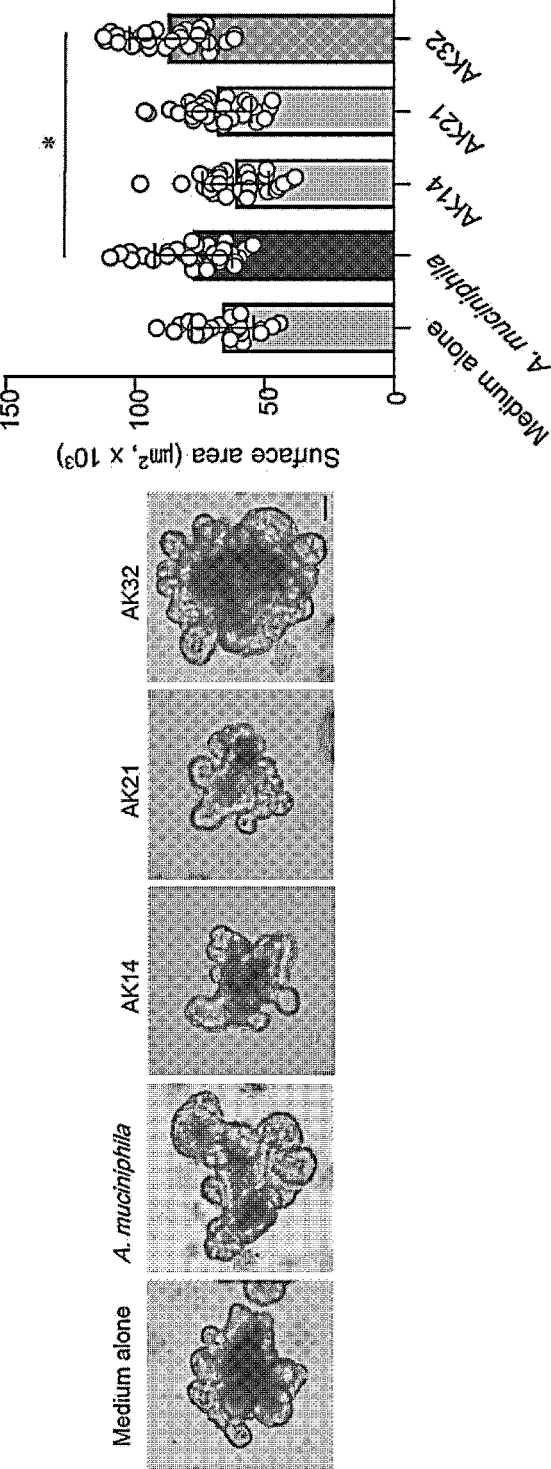
FIG. 1A shows the brightfield image and surface area of small intestine organoids treated with *Akkermansia muciniphila* (*A. muciniphila*) BAA-835 or culture supernatant of *A. muciniphila* strain AK14, AK21 or AK32 collected from stool (scale bar=50 μm).

The present invention provides an *Akkermansia muciniphila* (*A. muciniphila*) AK32 (Accession No. KCTC 14172BP) strain.

The present inventors named the novel strain *A. muciniphila* AK32, and deposited it under Accession No. KCTC 14172BP at the Korean Collection for Type Cultures, Korea Research Institute of Bioscience and Biotechnology (KRIBB), 181, Ipsin-gil, Jeongeup-si, Jeollabuk-do 56212, Republic of Korea on Apr. 20, 2020.

The *A. muciniphila* AK32 of the present invention may prevent or improve intestinal damage, but the present invention is not limited thereto.

The *A. muciniphila* AK32 of the present invention may produce a methylmalonyl CoA/oxaloacetate decarboxylase beta subunit (MMD) enzyme including an amino acid sequence represented by SEQ ID NO: 3, but the present invention is not limited thereto.

The *A. muciniphila* AK32 of the present invention may promote the proliferation of intestinal epithelial cells, but the present invention is not limited thereto.

In one embodiment of the present invention, it was confirmed that the AK32 strain of the present invention has excellent small intestine organoid proliferation ability, compared with other existing strains.

In addition, the present invention provides a pharmaceutical composition for preventing or treating intestinal damage, which includes the *A. muciniphila* AK32 strain or a culture thereof as an active ingredient.

The term "culture" used herein refers to all actions performed to grow microorganisms in suitable artificially controlled environmental conditions, and is a concept including "fermentation."

Cells of the "*Akkermansia muciniphila* (*A. muciniphila*) AK32" include not only live bacteria obtained from a culture medium, but also any processed form of lactic acid bacteria known to those of ordinary skill in the art, such as a cell lysate, a dry material or a frozen material, but the present invention is not limited thereto. In addition, the term "culture" used herein refers to a "fermentation solution," and includes a culture obtained in a liquid medium or a processed product derived from a filtrate (centrifuged supernatant) from which the strain is removed itself through filtration or centrifugation of the culture.

In the present invention, the intestinal damage may be one or more selected from the group consisting of radiation-induced intestinal damage, drug-induced intestinal damage, alcohol-induced intestinal damage, and intestinal damage caused by an inflammatory bowel disease, but the present invention is not limited thereto.

In the present invention, radiation reacts with water in cells to generate reactive oxygen species, and the toxicity caused thereby affects cells and tissue, thereby causing an inflammatory response. When normal tissue is exposed to radiation, cells with high radiation sensitivity, present in the normal tissue, particularly, vascular cells and immune cells are affected. These vascular cells and immune cells are representative cells involved in the inflammatory response. Therefore, among the side effects caused by radiation, the highest frequency is intestinal inflammation, for example, an inflammatory response such as enteritis or pneumonia. According to the present invention, the intestinal damage is the acute gastrointestinal syndrome (GIS).

In the present invention, the inflammatory bowel disease may be one or more selected from the group consisting of a duodenal ulcer, an intestinal obstruction, acute gastrointestinal bleeding, Crohn's disease, enteric Behcet's disease, pouchitis, irritable bowel syndrome, and ulcerative colitis, but the present invention is not limited thereto.

In the present invention, the improvement in intestinal function may be one or more effects selected from the group consisting of, for example, improving intestinal microbiota; proliferating the proliferation of beneficial intestinal bacteria; increasing the content of short-chain fatty acids in the intestine; inhibiting the proliferation of harmful bacteria; or inducing the proliferation of intestinal epithelial cells, but the present invention is not limited thereto.

The content of the *A. muciniphila* AK32 strain or culture thereof in the composition of the present invention can be appropriately regulated by symptoms of a disease, the severity of the symptoms, and a patient's condition. For example, the content may be 0.0001 to 99.9 wt %, or 0.001 to 50 wt % based on the total weight of the composition, but the present invention is not limited thereto. The content ratio is a value based on the dry amount after removing a solvent.

The pharmaceutical composition according to the present invention may further include a suitable carrier, excipient and diluent, which are conventionally used in the preparation of a pharmaceutical composition. The excipient may be, for example, one or more selected from the group consisting of a diluent, a binder, a disintegrant, a lubricant, an adsorbent, a humectant, a film-coating material, and a controlled-release additive.

The pharmaceutical composition according to the present invention may be formulated in the form of a powder, a granule, a sustained-release granule, an enteric granule, a liquid, an ophthalmic solution, an elixir, an emulsion, a suspension, a spirit, a troche, aromatic water, a lemonade, a tablet, a sustained-release tablet, an enteric tablet, a sublingual tablet, a hard capsule, a soft capsule, a sustained-release capsule, an enteric capsule, a pill, a tincture, a soft extract, a dry extract, a fluid extract, an injection, a capsule, a perfusate, a plaster, a lotion, a paste, a spray, an inhalant, a patch, a sterile injection, or an external preparation such as an aerosol according to a conventional method, and the external preparation may be formulated in a cream, a gel, a patch, a spray, an ointment, a plaster, a lotion, a liniment, a paste or a cataplasma.

The carrier, excipient and diluent, which may be included in the pharmaceutical composition according to the present invention, may include lactose, dextrose, sucrose, an oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil.

The pharmaceutical composition may be formulated with a diluent or an excipient such as a filler, an extender, a binder, a wetting agent, a disintegrant, a surfactant, which are conventionally used.

As additives for a tablet, powder, granule, capsule, pill and troche, excipients such as corn starch, potato starch, wheat starch, lactose, sucrose, glucose, fructose, dimannitol, precipitated calcium carbonate, synthetic aluminum silicate, calcium monohydrogen phosphate, calcium sulfate, sodium chloride, sodium bicarbonate, purified lanolin, microcrystalline cellulose, dextrin, sodium alginate, methylcellulose, sodium carboxymethylcellulose, kaolin, urea, colloidal silica gel, hydroxypropyl starch, hydroxypropyl methyl cellulose (HPMC) 1928, HPMC 2208, HPMC 2906, HPMC 2910, propylene glycol, casein, calcium lactate and Primojel; binders such as gelatin, gum arabic, ethanol, agar powder, cellulose acetate phthalate, carboxymethyl cellulose, carboxymethyl cellulose calcium, glucose, purified water, sodium caseinate, glycerin, stearic acid, sodium carboxymethylcellulose, sodium methylcellulose, methylcellulose, microcrystalline cellulose, dextrin, hydroxycellulose, hydroxypropyl starch, hydroxymethylcellulose, purified shellac, starch powder, hydroxypropylcellulose, hydroxypropylmethylcellulose, polyvinyl alcohol and polyvinylpyrrolidone; disintegrants such as hydroxypropylmethylcellulose, corn starch, agar powder, methylcellulose, bentonite, hydroxypropyl starch, sodium carboxymethylcellulose, sodium alginate, carboxymethyl cellulose calcium, calcium citrate, sodium lauryl sulfate, silicic anhydride, 1-hydroxypropyl cellulose, dextran, an ion exchange resin, polyvinyl acetate, formaldehyde-treated casein and gelatin, alginic acid, amylose, guar gum, sodium bicarbonate, polyvinylpyrrolidone, calcium phosphate, gelled starch, gum arabic, amylopectin, pectin, sodium polyphosphate, ethyl cellulose, sucrose, magnesium aluminum silicate, a di-sorbitol solution and light anhydrous silicic acid; and lubricants such as calcium stearate, magnesium stearate, stearic acid, hydrogenated vegetable oil, talc, lycopodium, kaolin, petrolatum, sodium stearate, cacao butter, sodium salicylate, magnesium salicylate, polyethylene glycol (PEG) 4000 and, PEG 6000, liquid paraffin, hydrogenated soybean oil (Lubri wax), aluminum stearate, zinc stearate, sodium lauryl sulfate, magnesium oxide, Macrogol, synthetic aluminum silicate, silicic anhydride, a higher fatty acid, a higher alcohol, silicone oil, paraffin oil, polyethylene glycol fatty acid ether, starch, sodium chloride, sodium acetate, sodium oleate, dl-leucine and light anhydrous silicic acid may be used.

Additives for a liquid according to the present invention may be water, diluted hydrochloric acid, diluted sulfuric acid, sodium citrate, monostearate sucrose, polyoxyethylene sorbitol fatty acid esters (Tween esters), polyoxyethylene monoalkylethers, lanolin ethers, lanolin esters, acetic acid, hydrochloric acid, aqueous ammonia, ammonium carbonate, potassium hydroxide, sodium hydroxide, prolamine, polyvinylpyrrolidone, ethyl cellulose, and sodium carboxymethylcellulose.

In the syrup according to the present invention, a sucrose solution, other sugars or sweeteners may be used, and if necessary, a fragrance, a coloring agent, a preservative, a stabilizer, a suspending agent, an emulsifier, or a thickening agent may be used.

As the emulsion according to the present invention, distilled water may be used, and if necessary, an emulsifier, a preservative, a stabilizer, or a fragrance may be used.

As the suspending agent according to the present invention, acacia, tragacanth, methylcellulose, carboxymethylcellulose, sodium carboxymethylcellulose, microcrystalline cellulose, sodium alginate, hydroxypropylmethylcellulose, HPMC 1828, HPMC 2906, or HPMC 2910 may be used, and if necessary, a surfactant, a preservative, a stabilizer, a coloring agent, or a fragrance may be used.

As the injection according to the present invention, a solvent such as injectable sterile water, 0.9% sodium chloride for injection, Ringer's solution, dextrose for injection, dextrose+sodium chloride for injection, PEG, lactated Ringer's solution, ethanol, propylene glycol, non-volatile oil-sesame oil, cottonseed oil, peanut oil, soybean oil, corn oil, ethyl oleate, isopropyl myristic acid or benzene benzoate; a solubilizing agent such as sodium benzoate, sodium salicylate, sodium acetate, urea, urethane, monoethylacetamine, butazolidine, propylene glycol, Tween, nicotinamide, hexamine or dimethylacetamide; a buffer such as a weak acid and a salt thereof (acetic acid and sodium acetate), a weak base and a salt thereof (ammonia and ammonium acetate), an organic compound, a protein, albumin, peptone, or gums; an isotonic agent such as sodium chloride; a stabilizer such as sodium bisulfite (NaHSO$_3$), carbon dioxide gas, sodium metabisulfite (Na$_2$S$_2$O$_5$), sodium sulfite (Na$_2$SO$_3$), nitrogen gas (N$_2$) or ethylenediaminetetracetic acid; an antioxidant such as sodium bisulfide 0.1%, sodium formaldehyde sulfoxylate, thiourea, disodium ethylenediaminetetraacetate or acetone sodium bisulfite; a pain-relief agent such as benzyl alcohol, chlorobutanol, procaine hydrochloride, glucose or calcium gluconate; or a suspending agent such as sodium CMC, sodium alginate, Tween 80 or aluminum monostearate, may be used.

As the suppository according to the present invention, a base such as cacao butter, lanolin, Witepsol, polyethylene glycol, glycerogelatin, methyl cellulose, carboxymethylcellulose, a mixture of stearate and oleate, Subanal, cottonseed oil, peanut oil, palm oil, cacao butter+cholesterol, lecithin, Lanette wax, glycerol monostearate, Tween or Span, Imhausen, monolene (propylene glycol monostearate), glycerin, Adeps solidus, Buytyrum Tego-G, Cebes Pharma 16, hexalide base 95, Cotomar, Hydrokote SP, S-70-XXA, S-70-XX75 (S-70-XX95), Hydrokote 25, Hydrokote 711, Idropostal, Massa estrarium (A, AS, B, C, D, E, I, T), Mass-MF, Masupol, Masupol-15, neosuppostal-N, paramount-B, supposiro (OSI, OSIX, A, B, C, D, H, L), suppository base IV types (AB, B, A, BC, BBG, E, BGF, C, D, 299), Suppostal (N, Es), Wecoby (W, R, S, M, Fs), or a Tegester triglyeride base (TG-95, MA, 57) may be used.

A solid formulation for oral administration may be a tablet, pill, powder, granule or capsule, and such a solid formulation may be prepared by mixing at least one of excipients, for example, starch, calcium carbonate, sucrose, lactose and gelatin, with the active ingredient. In addition to the simple excipient, lubricants such as magnesium stearate and talc may also be used.

As a liquid formulation for oral administration, a suspension, a liquid for internal use, an emulsion, or a syrup may be used, and a generally-used simple diluent such as water or liquid paraffin, as well as various types of excipients, for example, a wetting agent, a sweetener, a fragrance and a preservative may be included. A formulation for parenteral administration may be a sterilized aqueous solution, a non-aqueous solvent, a suspension, an emulsion, a lyophilizing agent or a suppository. As the non-aqueous solvent or suspension, propylene glycol, polyethylene glycol, a vegetable oil such as olive oil, or an injectable ester such as ethyl oleate may be used.

The pharmaceutical composition according to the present invention is administered at a pharmaceutically effective amount. In the present invention, the "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field.

The pharmaceutical composition of the present invention may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by one of ordinary skill in the art.

The pharmaceutical composition of the present invention may be administered into a subject via various routes. All administration routes may be expected, and the pharmaceutical composition of the present invention may be administered by, for example, oral administration, subcutaneous injection, intraperitoneal administration, intravenous, intramuscular or intrathecal injection, sublingual administration, buccal administration, rectal insertion, vaginal insertion, ocular administration, ear administration, nasal administration, inhalation, spraying through the mouth or nose, skin administration, or transdermal administration.

The pharmaceutical composition of the present invention is determined according to the type of drug as an active ingredient as well as several related parameters such as a disease to be treated, an administration route, a patient's age, sex and body weight, and the severity of a disease.

The term "subject" used herein refers to a target in need of treatment, and more specifically, a mammal such as a human or a non-human primate, a mouse, a rat, a dog, a cat, a horse, or a cow, but the present invention is not limited thereto.

The "administration" used herein refers to providing the composition of the present invention to a subject by any suitable method.

The "prevention" used herein refers to all actions of inhibiting or delaying the occurrence of a target disease, and the "treatment" used herein refers to all actions involved in alleviating or beneficially changing symptoms by the administration of the pharmaceutical composition according to the present invention, and the "improvement" used herein refers to all actions of reducing the parameters associated with a target disease, for example, the severity of symptoms, by the administration of the composition according to the present invention.

In addition, the present invention provides a food composition for preventing or improving intestinal damage, which includes the *A. muciniphila* AK32 stain or a culture thereof as an active ingredient.

In addition, the present invention provides a food composition for improving intestinal function, which includes the *A. muciniphila* AK32 stain or a culture thereof as an active ingredient.

When the *A. muciniphila* AK32 strain of the present invention or a culture thereof is used as a food additive, the *A. muciniphila* AK32 strain or culture thereof may be added alone or used in combination with another food or food ingredient, and suitably used according to a conventional method. The mixed amount of the active ingredient may be suitably determined according to the purpose of use (for prevention, health or therapeutic treatment). Generally, in the preparation of foods or beverages, the *A. muciniphila* AK32 strain of the present invention or a culture thereof may be added at 15 wt % or less, or 10 wt % or less with respect to a raw material. However, in the case of long-term ingestion for health and hygiene purposes or health control, the amount may be less than the above range, and since there is no problem in terms of safety, the active ingredient may be used in an amount more than the above range.

There is no particular limitation to the type of food. Examples of the food to which the material can be added may include meat, sausage, bread, chocolate, candy, snacks, confectionaries, pizza, ramen, other noodles, gum, dairy products including ice cream, various types of soups, beverages, tea, drinks, alcoholic beverages and vitamin complexes, and in a general sense, include all health functional foods.

The health beverage composition according to the present invention may contain various flavoring agents or natural carbohydrates as additional ingredients like a conventional beverage. Examples of the above-mentioned natural carbohydrates include conventional sugars, for example, monosaccharides such as glucose, fructose, etc.; disaccharides such as maltose, sucrose, etc.; and polysaccharides such as dextrin, cyclodextrin, etc., and sugar alcohols such as xylitol, sorbitol, erythritol, etc. As the sweeteners, natural sweeteners such as thaumatin and a stevia extract, or synthetic sweeteners such as saccharin and aspartame may be used. In general, the proportion of the natural carbohydrate is approximately 0.01 to 0.20 g, or 0.04 to 0.10 g per 100 mL of the composition of the present invention.

The composition of the present invention may contain various nutrients, vitamins, electrolytes, flavoring agents, coloring agent, pectic acid and a salt thereof, alginic acid and a salt thereof, organic acids, protective colloidal thickening agents, pH adjusters, stabilizers, preservatives, glycerin, alcohols, or carbonation agents used in carbonated beverages. Other than these, the composition of the present invention may contain fruit pulp for producing natural fruit juices, fruit drinks and vegetable drinks. These components may be used independently or in combination. The proportion of the additive is not very important, but may generally be selected in the range of 0.01 to 0.20 parts by weight with respect to 100 parts by weight of the composition of the present invention.

In addition, the present invention provides a probiotic, which includes the *A. muciniphila* AK32 strain or a culture thereof.

In addition, the present invention provides a composition for an intestinal drug, which includes the *A. muciniphila* AK32 strain or a culture thereof as an active ingredient.

In addition, the present invention provides a probiotic product composition, which includes the *A. muciniphila* AK32 strain or a culture thereof as an active ingredient.

In addition, the present invention provides a food additive composition, which includes the *A. muciniphila* AK32 strain or a culture thereof as an active ingredient.

The *A. muciniphila* AK32 strain of the present invention may be live bacteria or probiotics, and may be used for improving the intestinal health of a human and an animal, that is, an intestinal drug, a probiotic product or a food additive composition. The composition may include the strain itself, a lysate thereof, or the strain culture as an active ingredient, and further include an excipient or carrier.

The composition includes the culture in which the strain is cultured in a liquid medium, and a filtrate (supernatant obtained after centrifugation) from which the strain is removed through filtration or centrifugation of the culture. The content of the *A. muciniphila* AK32 strain in the composition may vary depending on the use and formulation of the composition. The composition for an intestinal drug or probiotic product according to the present invention may be prepared and administered by various formulations and methods. For example, the *A. muciniphila* AK32, the lysate thereof, or the culture thereof may be mixed with a carrier and a fragrance, which are conventionally used in the pharmaceutical field, to be prepared and administered in the form of a tablet, a troche, a capsule, an elixir, a syrup, a powder, a suspension, or a granule.

As the carrier, a binder, a lubricant, a disintegrant, an excipient, a solubilizer, a dispersant, a stabilizer, or a suspending agent may be used. An administration method may be oral or parenteral administration, or a coating method, and preferably, oral administration. In addition, the dosage may be appropriately selected according to the absorption, inactivation rate and excretion rate of an active ingredient in the body, and a patient's age, sex and condition. In addition, a composition for feed according to the present invention may be prepared in the form of fermented feed, compound feed, a pellet and silage. The fermented feed may be prepared by fermenting an organic material by adding the *A. muciniphila* AK32 strain of the present invention and various microorganisms or enzymes, and the compound feed may be prepared by mixing various types of general feed and the *A. muciniphila* AK32 of the present invention. The pellet-type feed may be prepared by formulating the fermented feed or compound feed in a pellet form, and the silage may be prepared by fermenting green forage using the *A. muciniphila* AK32 according to the present invention.

The *A. muciniphila* AK32 according to the present invention or the culture thereof may be used as a food additive for foods such as kimchi, beverages, baby food, fermented milk, and bread. In addition, the *A. muciniphila* AK32 of the present invention or the culture thereof may be used as a starter for preparing a fermented product. The fermented product includes cheese, kimchi, and a fermented raw product. The fermented product using the *A. muciniphila* AK32 of the present invention or the culture thereof may be prepared by a method conventionally known in the art. For example, after treating a grain powder such as brain rice or adlay with the *A. muciniphila* AK32 according to the present invention or 2 or 3 types of mixed lactic acid bacteria including the same and fermenting the processed product at an appropriate temperature, fermented raw products may be manufactured by suitably mixing various agricultural products such as white rice, glutinous rice and millet to have excellent nutritional balance and palatability.

In addition, the present invention provides a method of preventing, improving or treating intestinal damage, which includes administering a composition including the *A. muciniphila* AK32 strain or a culture thereof into a subject.

In addition, the present invention provides a use of a composition including the *A. muciniphila* AK32 strain or a culture thereof for prevention, improvement or treatment of intestinal damage.

In addition, the present invention provides a use of the *A. muciniphila* AK32 strain or a culture thereof for production of a drug used for intestinal damage.

As the present invention may have various modifications and embodiments, specific embodiments of the present invention will be described in further detail below. However, the present invention is not limited to the specific embodiments, and it should be understood that the present invention includes all modifications, equivalents and alternatives included in the technical idea and scope of the present invention. To describe the present invention, when it is determined that a detailed description of the related art may obscure the gist of the present invention, the detailed description thereof will be omitted.

Hereinafter, to help in understanding the present invention, exemplary examples will be suggested. However, the following examples are merely provided to more easily understand the present invention, and not to limit the present invention.

EXAMPLES

Experimental Example 1. Experimental Method

Experimental Example 1-1. Preparation of Mouse

All animals used in the examples of the present invention were 8 to 10-week-old female mice, and fed sterile food and water ad libitum. C57BL/6 mice were purchased from OrientBio (Korea). The mice were housed in an animal facility of the Asan Medical Center (Korea) and bred under conditions free from specific pathogens. All animal experiments were approved by the Institutional Animal Care and Use Committee of the Asan Medical Center (Approval No. 2019-12-251). All experiments were performed according to the related guidelines and regulations.

Experimental Example 1-2. Isolation of *A. muciniphila* Strain from Human Stool 11 novel strains of *A. muciniphila* were isolated from human stools of a total of 32 healthy volunteers. The stool was dissolved in PBS, and seeded in a 0.4% mucin-added BHI agar medium (KisanBio) without dextrose at 37° C. under anaerobic conditions using a GasPak 100 system (BD Bioscience). *A. muciniphila* was selected and confirmed by PCR using the primer set, 5'-CAGCACGT-GAAGGTGGGGAC-3' (SEQ ID NO: 1) and 5'-CCTTGCGGTTGGCTTCAGAT-3' (SEQ ID NO: 2).

Experimental Example 1-3. Oral Administration of *A. muciniphila*

*A. muciniphila* (ATCC BAA-835T) and a newly isolated *A. muciniphila* AK32 strain were cultured in brain heart infusion media (BD Bioscience) supplemented with 0.4% mucin (Sigma) and cultured under an anaerobic condition using the GasPak 100 system (BD Bioscience) at 37° C. The cultures were concentrated and suspended in anaerobic PBS, and then administered to mice ($8 \times 10^8$ CFU per dose) every day for 4 weeks using a Zonde needle for oral use.

Experimental Example 1-4. Crypt Isolation

The small intestine (SI) was opened longitudinally and washed with PBS. To dissociate crypts, tissue was incubated in 1 mM EDTA in PBS at 4° C. for 30 minutes, washed in PBS, and then transferred to 5 mM EDTA in PBS for an additional 1-hour incubation at 4° C. Subsequently, samples were then suspended in PBS and filtered by a 70 μm cell strainer (BD Falcon).

Experimental Example 1-5. Organoid Culture

For organoid culture, 200 to 500 crypts per well were suspended in Matrigel (Corning).

Complete ENR medium (Noggin-supplemented ER medium) containing advanced DMEM/F12 (Gibco), 100× penicillin/streptomycin (Gibco), 1 mM N-acetyl cysteine (Sigma-Aldrich), B27 supplement (Thermo Fisher Scientific), N2 supplement (Thermo Fisher Scientific), EGF (Thermo Fisher Scientific), Noggin (R & D Systems), and R-spondin-1-conditioned medium was used. The ENR medium was replaced every 2 to 3 days. The surface areas of the organoids were measured using a microscope by taking several random non-overlapping photos of the organoids in a well using an inverted microscope (Carl Zeiss). Each photo was analyzed using ImageJ software (NIH) and the Zen image program (Carl Zeiss). Oraganoid perimeters for area measurements were measured manually or automatically using ImageJ software.

Experimental Example 1-6. Histology

Ileum tissue of the small intestine was removed and opened longitudinally. Subsequently, the tissue was formed by Swiss rolls, fixed in 4% paraformaldehyde (PFA) and embedded in paraffin. Tissue sections were stained with hematoxylin-eosin (H & E) or periodic acid-Schiff (PAS).

Experimental Example 1-7. Treatment of Organoids with Cecal Contents 100 mg each of cecal contents was diluted in 1 ml of serum-free DMEM/F12 (Gibco) medium and vortexed for 1 hour. The contents were centrifuged at 4,000 rpm for 10 minutes, and supernatants were passed through a 0.22-μm syringe filter (Pall Corporation). To address the effect on the composition of cecal contents, an ENR medium was supplemented with a 0.01% supernatant of the cecal contents suspended in advanced DMEM/F12. A Gpr43 antagonist (GLPG0974, 0.1 μM, Tocris) and a Gpr41 antagonist (β-hydroxy butyrate, 3 mM, Sigma) were used.

Experimental Example 1-8. Whole Genome Sequencing

Agarose gel electrophoresis was performed to test the integrity of gDNA, and gDNA was quantified using Quant-IT PicoGreen (Invitrogen). Subsequently, a sequencing library was prepared according to the manufacturer's instructions for 20-kb template preparation using the PacBio DNA template Prep kit 1.0. The library was quantified using the Quant-IT PicoGreen, and vertified using a high-sensitivity DNA chip (Agilent Technologies). Subsequently, the library was sequenced using PacBio P6C4 chemistry in 8-well-SMART Cell v3 in PacBio RSII. The genome of AK32 was constructed using new PacBio sequencing data. Subsequently, sequencing analysis was performed by Chunlab, Inc. PacBio sequencing data was collected with PacBio SMRT Analysis 2.3.0 using the HGAP2 protocol (Pacific Biosciences). The resulting product obtained from the PacBio sequencing data was circularized using Circlator 1.4.0 (Sanger Institute). The gene-finding and functional annotation pipeline of the whole genome used the Ezbio-Cloud genome database. A protein-coding sequence was predicted by Prodigal 2.6.2. Genes encoding tRNA were searched for using tRNAscan-SE 1.3.1. Rfam and other non-coding RNA were searched for in the Rfam 12.0 database. A comparative whole genome was studied by average nucleotide identity base BLAST (ANIb). The ANIb value was calculated by an ANI calculator of the Kostas lab (http://enve-omics.ce.gatech.edu/ani).

Experimental Example 1-9. Real-Time PCR

Total RNA from the small intestine and organoids was extracted using a RNeasy mini kit (Qiagen), and cDNA was synthesized using Superscript II reverse transcriptase and oligo dT primers (Thermo Fisher Scientific). Total RNA of *A. muciniphila* was extracted using Trizol (Thermo Fisher Scientific). For cDNA synthesis using bacterial RNA, a gDNA remover (Toyobo) and the ReverTra Ace qPCR RT Master Mix were used. cDNA was used as a template for real-time PCR performed using SYBR green chemistry (Affymetrix) on a Real-time PCR system (Applied Biosystems).

The primers used here are as follows: Muc2, 5'-CCT-TAGCCAAGGGCTCGGAA-3' (SEQ ID NO: 4) and 5'-GGCCCGAGAGTAGACCTTGG-3' (SEQ ID NO: 5); Lyz1, 5'-ATGGCGAACACAATGTCAAA-3' (SEQ ID NO: 6) and 5'-GCCCTGTTTCTGCTGAAGTC-3' (SEQ ID NO: 7); Wnt3, 5'-CTTCTAATGGAGCCCCACCT-3' (SEQ ID NO: 8) and 5'-GAGGCCAGAGATGTGTACTGC-3' (SEQ ID NO: 9); Axin2, 5'-AACCTATGCCCGTTTCCTCT-3' (SEQ ID NO: 10) and 5'-GAGTGTAAAGACTTGGTCCA-3' (SEQ ID NO: 11); Ctnnb1, 5'-ATG-GAGCCGGACAGAAAAGC-3' (SEQ ID NO: 12) and 5'-TGGGAGGTGTCAACATCTTC-3' (SEQ ID NO: 13); Lgr5, 5'-CCTGTCCAGGCTTTCAGAAG-3' (SEQ ID NO: 14) and 5'-CTGTGGAGTCCATCAAAGCA-3' (SEQ ID NO: 15); β-actin, 5'-TGGAATCCTGTGGCATCCAT-GAAAC-3' (SEQ ID NO: 16) and 5'-TAAAACGCAGCTCAGTAACAGTCCG-3' (SEQ ID NO: 17); pdh, 5'-AACCGATTATTGAAGCGGCA-3' (SEQ ID NO: 18) and 5'-ATATTGGCGGCTTCGTGAAA-3' (SEQ ID NO: 19); mmd, 5'-GAC-CAAGAAGGAACGCCTCA-3' (SEQ ID NO: 20) and 5'-GTTCCGTCACCTTGCATTCG-3' (SEQ ID NO: 21); Universal 16S rDNA, 5'-ACTCCTACGGGAGGCAGCAG-3' (SEQ ID NO: 22) and 5'-ATTACCGCGGCTGCTGG-3' (SEQ ID NO: 23); and *A. muciniphila* 16S rDNA, 5'-CAGCACGTGAAGGTGGGGAC-3' (SEQ ID NO: 24) and 5'-CCTTGCGGTTGGCTTCAGAT-3' (SEQ ID NO: 25).

14

Experimental Example 1-10. Quantitative Measurement of Short-Chain Fatty Acid (SCFA)

All reagents and solvents for metabolite analysis were purchased from Sigma. Mouse cecal contents (10-20 mg) were vigorously homogenized with 400 μL of an internal standard solution [1 mM propionic acid $(C_3)$-d6, and 100 μM butyric acid $(C_4)$-d$_7$]. For analysis of a bacterial culture supernatant, 100 μL of a culture supernatant was mixed with 200 μL of the internal standard solution. After centrifugation, the supernatant was filtered and eliminated. Dichloromethane containing AABD-SH (20 μL, 20 mM), triphenylphosphine (TPP; 20 μL, 20 mM) and 2,2-dipyridyl disulfide (DPDS; 20 μL) was added to the filtrate. The solution was incubated for 10 minutes at room temperature while vortexing, and dried under vacuum. The sample was reconstituted with 80 μL methanol to prepare for LC-MS/MS analysis. An LC-MS/MS system equipped with 1290 HPLC (Agilent Technologies, Denmark), Qtrap 5500 (AB-Sciex) and a reverse-phase column (Pursuit 5 C18 150×2.0 mm, Agilent Technologies) was used. The extracted ion chromatogram (EIC) corresponding to a specific transition for each metabolite was used for quantification. The area under the curve of each EIC was normalized to the EIC area of the internal standard. The peak area ratio of each metabolite to the internal standard was normalized using serum volume or tissue weight in a sample, and then used for relative comparison.

Experimental Example 1-11. Statistical Analysis

Statistical analysis was performed using Prism software (GraphPad, La Jolla, CA). A two-tailed t-test was used for pairwise and two independent groups comparisons. Data was expressed as means±SEM, and $p<0.05$, $p<0.01$, and $p<0.001$ were considered statistically significant.

Example 1. Isolation and Deposition of *A. muciniphila* AK32 Strain

To discover a better *A. muciniphila* strain than the types of strains (i.e., ATCC BAA-835[7]) commonly used in ISC-mediated epithelial development, *A. muciniphila* was isolated from the stool of a healthy human. Using selective media and species-specific PCR, three *A. muciniphila* strains (AK14, AK21, AK32) were obtained.

To evaluate the effect of the isolated *A. muciniphila* strain on ISC-mediated epithelial development, a screening system using intestinal organoids in the presence of culture supernatants obtained from each isolated strain was selected.

As shown in FIG. 1A, it was confirmed that only the culture supernatant of AK32 among three newly isolated strains significantly increased the organoid size compared to the existing *A. muciniphila* or other isotype strains.

That is, among the three isolated strains, the *A. muciniphila* AK32 strain was finally determined as the best strain according to the following examples, and named *A. muciniphila* AK32 (AK32; Accession No. KCTC 14172BP).

Example 2. Confirmation of Effect of Improving Intestinal Damage of *A. muciniphila* AK32 Strain First, to determine whether the ISC-mediated epithelial development increased by AK32 depends on SCFA, a Gpr41/43 antagonist was selected.

Figure 1B:
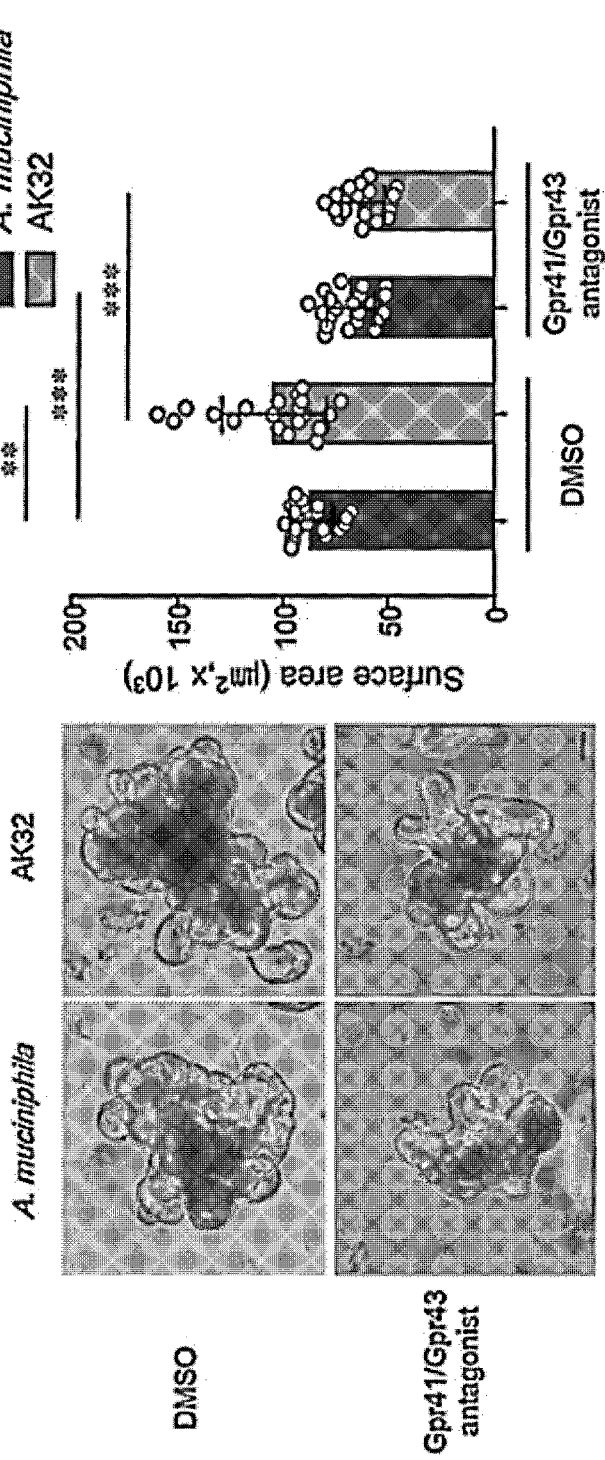
FIG. 1B shows the brightfield image and surface area of small intestine organoids treated with a culture supernatant in the presence or absence of a Gpr41/Gpr43 antagonist (scale bar=50 μm).

As shown in FIG. 1B, in the group using the Gpr41/43 antagonist, the sizes of intestinal organoids upregulated by the culture supernatant of AK32 were significantly reduced.

Figure 1C:
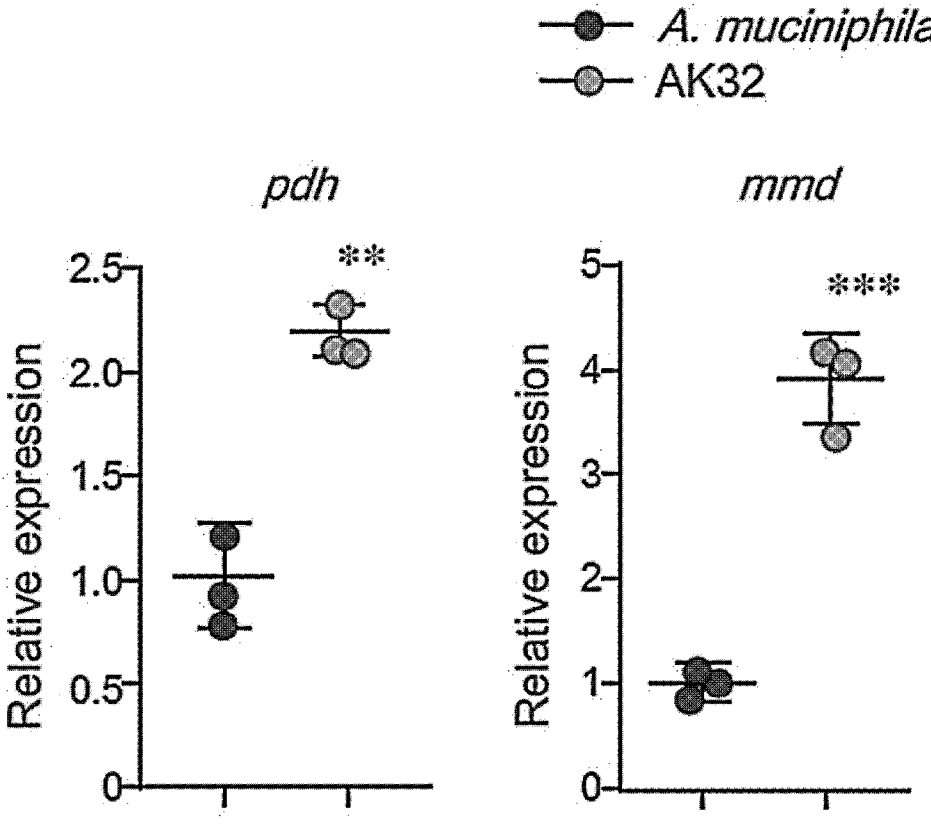
FIG. 1C shows the result of measuring the mRNA expression levels of a pyruvate dehydrogenase (PDH) E1 component and a methylmalonyl CoA/oxaloacetate decarboxylase beta subunit (MMD).

In addition, as shown in FIG. 1C, it was confirmed that the expression of enzymes affecting SCFA secretion in the AK32 strain, such as pyruvate dehydrogenase (pdh) E1 component and Na+ translocating methymalonyl-CoA/oxaloacetate decarboxylase (mmd), is significantly higher than that of the conventional ATCC BAA-835$^T$ strain.

Figure 1D:
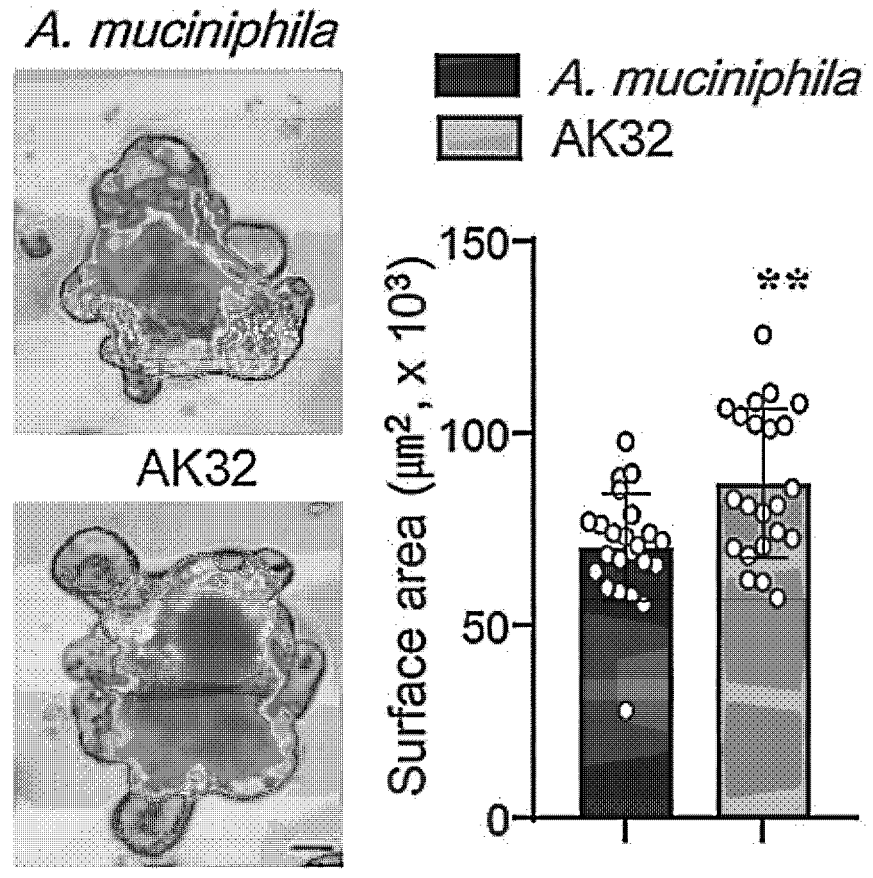
FIG. 1D shows the brightfield image and surface area of small intestine organoids of *A. muciniphila* BAA-835 or AK32-fed mice (scale bar=50 μm).

In addition, as shown in FIG. 1D, to further confirm the in vivo upregulatory function of the AK32 strain, mice were fed AK32 or typical *A. muciniphila* ATCC BAA-835$^T$ for 4 weeks.

Interestingly, it was shown that, compared to the conventional ATCC BAA-835$^T$-fed mice, the sizes of intestinal organoids in the AK32 strain-fed mice are significantly increased.

Figure 1E:
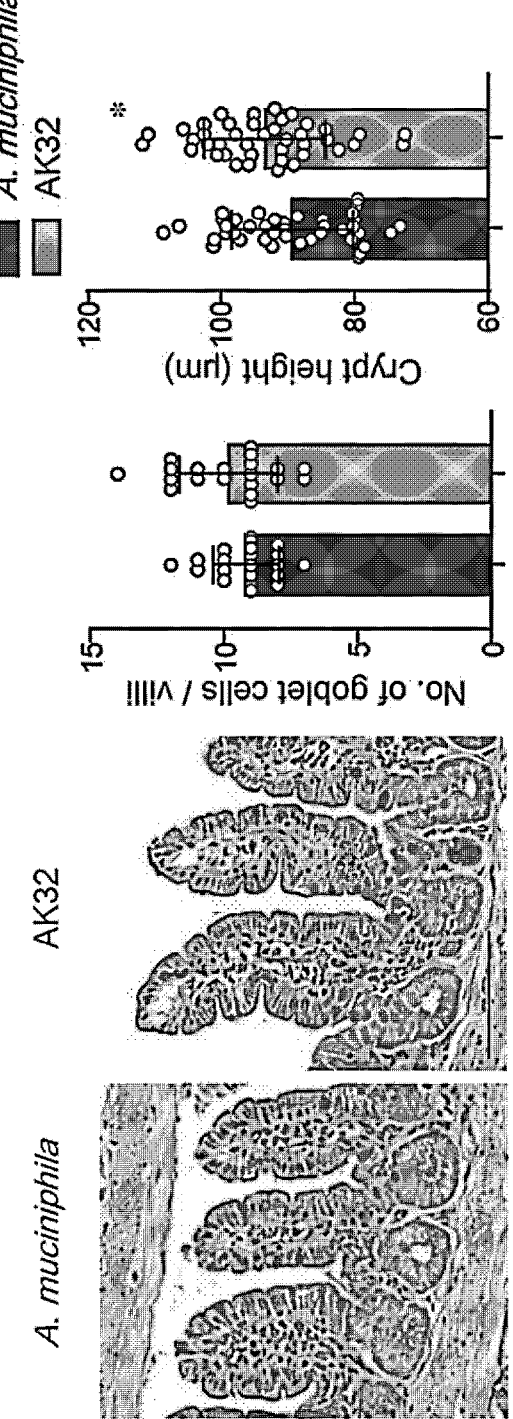
FIG. 1E shows the number of goblet cells and crypt height in the small intestine of *A. muciniphila* BAA-835 or AK32-fed mice (scale bar=10 μm).

In addition, as shown in FIG. 1E, it was shown that, compared to the ATCC BAA-835$^T$ the AK32-fed mice are increased in crypt height and the number of mucous-producing goblet cells in the small intestine.

Figure 1F:
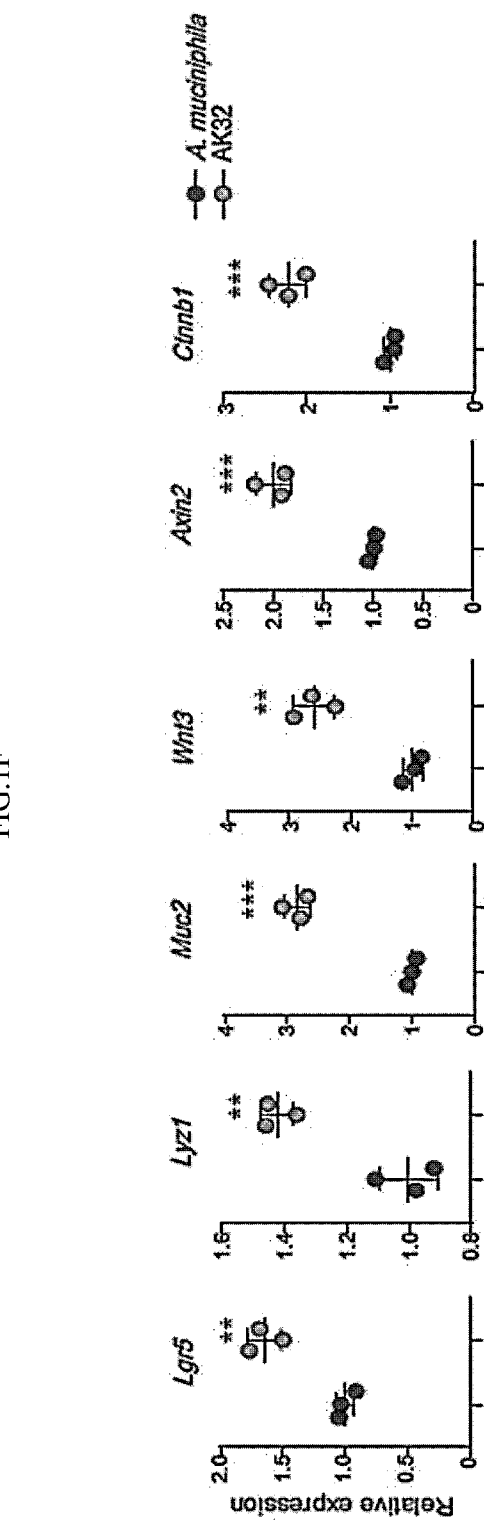
FIG. 1F shows the result of measuring the mRNA levels of Lgr5, Lyz1, Muc2, Wnt3, Axin2 and Ctnnb1 in the small intestine tissue of an AK32 strain-fed mouse.

In addition, as shown in FIG. 1F, it was shown that, compared to the ATCC BAA-835$^T$, the AK32-fed mice are significantly increased in mRNA expression levels of Lgr5, Lyz1, Muc2, Wnt3, Axin2, and Ctnnb1 in the small intestine.

In addition, FIG. 2 shows the complete genome map of the AK32 strain.

In addition, in FIGS. 3A and 3B, the amino acid sequences of PDH (FIG. 3A) and MMD (FIG. 3B) of the AK32 strain and the BAA-835 strain were compared, and showed different MMD sequences.

In addition, Table 1 below shows the results of analyzing the genome function information (genome annotation) of the AK32 strain and the BAA-835 strain.

TABLE 1

| Strain | Base (bp) | No. of CDS$^a$ | GC contents (%) | tRNA | rRNA | ANIb$^b$ (%) |
|---|---|---|---|---|---|---|
| *A. muciniphila* BAA-835 | 2,664,102 | 2,184 | 55.8 | 53 | 9 | — |

TABLE 1-continued

| Strain | Base (bp) | No. of CDS$^a$ | GC contents (%) | tRNA | rRNA | ANIb$^b$ (%) |
|---|---|---|---|---|---|---|
| *A. muciniphila* AK32 | 3,004,919 | 2,600 | 55.3 | 56 | 9 | 97.39 |

$^a$Coding sequences
$^b$Average nucleotide identity based BLAST to type strain BAA-835.

From the above results, it can be seen that the newly discovered AK32 strain has a characteristic genome in terms of ISC-mediated epithelial development, has an excellent effect compared to the conventional *A. muciniphila* strain, and this effect was by far the best among the strains.

Example 3. Confirmation of SCFA Secretion Promoting Effect of *A. muciniphila* AK32 Strain Since microorganism-derived metabolites are a key factor for maintaining intestinal homeostasis, SCFAs in *A. muciniphila* AK32 and BAA-835 cultures were compared, and after oral administration to mice for 4 weeks, SCFA levels in cecal contents were compared.

Figure 4A:
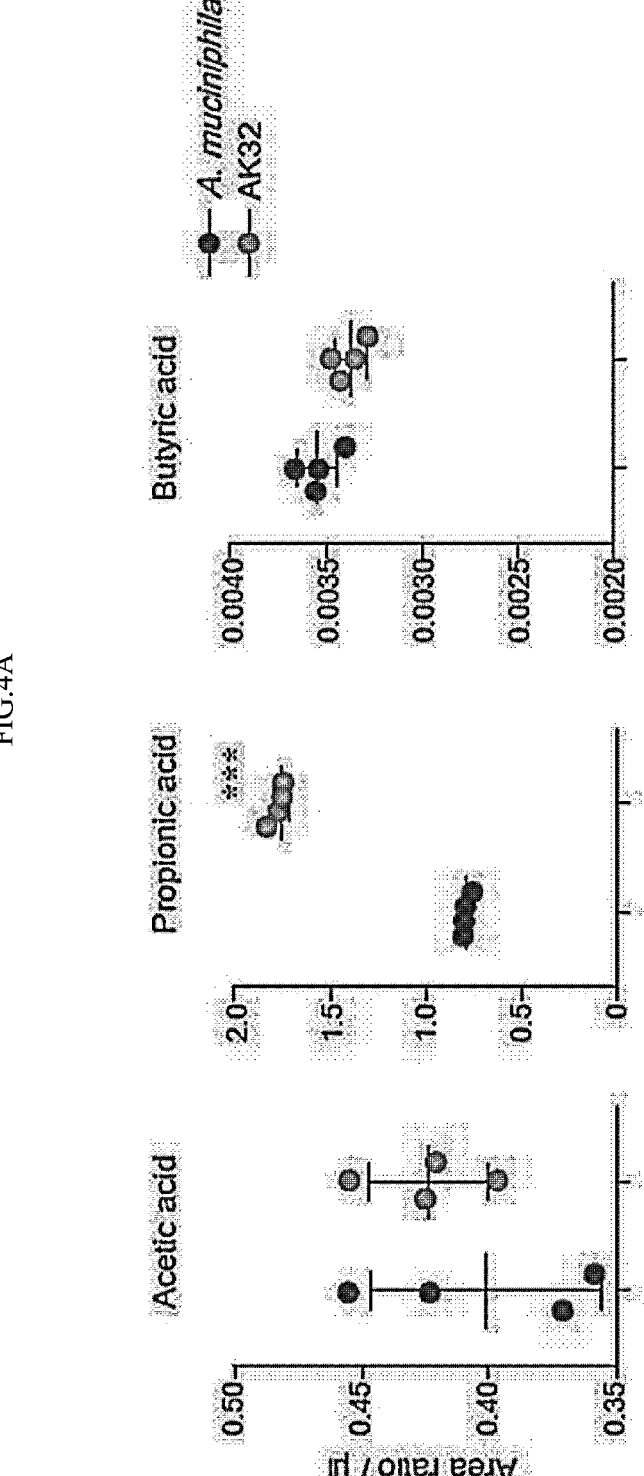
FIG. 4A shows the comparison in SCFA in bacterial cultures between the AK32 strain and the BAA-835 strain.

As a result, as shown in FIGS. 4A and 4B, it was confirmed that the AK32 strain of the present invention exhibits an excellent effect of promoting SCFA secretion, similar to or higher than that of the BAA-835$^T$ strain.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

The *Akkermansia muciniphila* AK32 (Accession No. KCTC 14172BP) strain of the present invention is expected to be effectively used in preparation of foods, pharmaceuticals, intestinal drugs, probiotic products and probiotics for preventing, improving or treating intestinal damage.

The invention claimed is:

1. A method for improving intestinal function, the method comprising:

administering to a subject an effective amount of *Akkermansia muciniphila* strain AK32 or a culture thereof as an active ingredient;

wherein the *Akkermansia muciniphila* AK32 strain is the strain deposited at the Korean Collection for Type Cultures, Korea Research Institute of Bioscience and Biotechnology (KRIBB), 181, Ipsin-gil, Jeongeup-si, Jeollabuk-do 56212, Republic of Korea, on Apr. 20, 2020, under Accession No. KCTC 14172BP.

2. The method of claim 1, wherein the *Akkermansia muciniphila* AK32 strain produces a methylmalonylCoA/oxaloacetate decarboxylase beta subunit (MMD) enzyme set forth in SEQ ID NO: 3.

3. The method of claim 1, wherein the *Akkermansia muciniphila* AK32 strain promotes the proliferation of intestinal epithelial cells.

* * * * *

SEQUENCE LISTING

```
<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
cagcacgtga aggtggggac                                              20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
```

-continued ccttgcggtt ggcttcagat                                                          20

<210> SEQ ID NO 3
<211> LENGTH: 553
<212> TYPE: PRT
<213> ORGANISM: Artificial Sequence
<220> FEATURE:
<223> OTHER INFORMATION: AK32 MMD (Na+ translocating methymalonyl-
      CoA/oxaloacetate decarboxylase)

<400> SEQUENCE: 3

Met Ser Leu Phe Asp Ser Leu Ile Thr Phe Leu Gln Gly Met Gly Val
1               5                   10                  15

Phe Ser Leu Ser Trp Gln Met Val Gly Met Trp Gly Ile Ala Ile Leu
            20                  25                  30

Leu Leu Tyr Leu Gly Val Ala Lys Gln Tyr Glu Pro Leu Leu Met Val
        35                  40                  45

Pro Ile Ala Phe Gly Ala Leu Ile Ala Asn Ile Pro Asp Asn Gly Met
    50                  55                  60

Leu Ile Thr Gln Leu Asn Gln Gln Val Ile Ser Ser Asn Glu Gln Gly
65                  70                  75                  80

Glu Val Thr Ser Thr Ser Leu Asn Asn Val Gly Tyr Leu Arg Val His
                85                  90                  95

Val Ala Pro Leu Gln Gln Thr Pro Ala Lys Val Pro Ala Asn Leu Thr
            100                 105                 110

Thr Pro Glu Ala Arg Ala Gln Tyr Leu Glu Thr Met Gln Gln Pro Met
        115                 120                 125

Gln Val Tyr Pro Gly Ser Gln Leu Thr Val Ser Lys Ile Lys Ser Val
    130                 135                 140

Arg Glu Ser Gln Glu Lys Ala Lys Ala Asp Ala Ala Arg Leu Gly Asp
145                 150                 155                 160

Asp Ser Leu Thr Val Asp Pro Asn Leu Lys Asp Phe Gln Asn Val Glu
            165                 170                 175

Asp Asn Gly Asn Glu Pro Val Phe Leu Leu Thr Asn Gly Glu Gly Thr
        180                 185                 190

Thr Val Val Arg Gln Gln Gly Val Asn Tyr Phe Asp Thr Ser Gly Asn
        195                 200                 205

Arg Val Pro Val Asp Leu Lys Thr Gln Lys Leu Glu Pro Leu Val Val
    210                 215                 220

Ser Ala Ala Gly Lys Tyr Val Ala Val Gly Gln His Thr Gln Glu Leu
225                 230                 235                 240

Leu Val Thr Ser Ile His Gly Gly Leu Tyr Asp Trp Ile Gly Leu Gly
            245                 250                 255

Ile Lys Ala Glu Ile Phe Pro Pro Ile Ile Phe Leu Gly Val Gly Ala
        260                 265                 270

Leu Thr Asp Phe Gly Pro Leu Leu Ala Ala Pro Arg Thr Leu Leu Leu
    275                 280                 285

Gly Ala Ala Ala Gln Val Gly Val Ala Ala Thr Phe Phe Met Ala Leu
    290                 295                 300

Phe Met Gly Phe Asn Pro Asn Glu Ala Ala Ser Ile Gly Ile Ile Gly
305                 310                 315                 320

Gly Ala Asp Gly Pro Thr Ser Ile Phe Leu Thr Met Lys Leu Ala Pro
            325                 330                 335

His Leu Leu Gly Ala Val Ala Val Ala Ala Tyr Thr Tyr Met Ser Leu
            340                 345                 350

-continued

```
Val Pro Leu Ile Gln Pro Pro Ile Met Ala Leu Leu Thr Thr Lys Lys
        355                 360                 365

Glu Arg Leu Ile Arg Met Lys Ser Leu Arg Thr Val Ser Lys Ser Glu
        370                 375                 380

Lys Leu Phe Phe Ala Val Leu Val Thr Ile Val Thr Ile Leu Leu Ile
385                 390                 395                 400

Pro Asp Ala Ser Pro Leu Ile Gly Met Leu Met Leu Gly Asn Phe Leu
                405                 410                 415

Arg Glu Cys Lys Val Thr Glu Arg Leu Val Gln Ala Ser Gln Asn Glu
                420                 425                 430

Ile Ile Asn Ile Val Thr Ile Phe Leu Gly Thr Ser Val Gly Leu Thr
        435                 440                 445

Met Gln Gly Asp Arg Phe Leu Gln Ala Glu Thr Leu Leu Ile Ile Leu
        450                 455                 460

Leu Gly Ile Val Ala Phe Gly Val Ala Thr Ala Gly Gly Val Ile Ala
465                 470                 475                 480

Ala Lys Leu Met Asn Leu Ile Trp Arg Lys Asn Pro Val Asn Pro Leu
                485                 490                 495

Ile Gly Ser Ala Gly Val Ser Ala Val Pro Met Ala Ala Arg Val Ser
                500                 505                 510

His Asn Val Gly Gln Lys Tyr Asp Pro Ser Asn Tyr Leu Leu Met His
        515                 520                 525

Ala Met Gly Pro Asn Val Ala Gly Val Ile Gly Thr Ala Val Ile Ala
        530                 535                 540

Gly Tyr Tyr Ile Ala Thr Leu Ala Lys
545                 550
```

```
<210> SEQ ID NO 4
<211> LENGTH: 20
<212> TYPE: DNA
<213> ORGANISM: Artificial Sequence
<220> FEATURE:
<223> OTHER INFORMATION: Muc2 forward primer

<400> SEQUENCE: 4
ccttagccaa gggctcggaa                                                          20

<210> SEQ ID NO 5
<211> LENGTH: 20
<212> TYPE: DNA
<213> ORGANISM: Artificial Sequence
<220> FEATURE:
<223> OTHER INFORMATION: Muc2 reverse primer

<400> SEQUENCE: 5
ggcccgagag tagaccttgg                                                          20

<210> SEQ ID NO 6
<211> LENGTH: 20
<212> TYPE: DNA
<213> ORGANISM: Artificial Sequence
<220> FEATURE:
<223> OTHER INFORMATION: Lyz1 forward primer

<400> SEQUENCE: 6
atggcgaaca caatgtcaaa                                                          20

<210> SEQ ID NO 7
<211> LENGTH: 20
<212> TYPE: DNA
```

<213> ORGANISM: Artificial Sequence
<220> FEATURE:
<223> OTHER INFORMATION: Lyz1 reverse primer

<400> SEQUENCE: 7
gccctgtttc tgctgaagtc                                              20

<210> SEQ ID NO 8
<211> LENGTH: 20
<212> TYPE: DNA
<213> ORGANISM: Artificial Sequence
<220> FEATURE:
<223> OTHER INFORMATION: Wnt3 forward primer

<400> SEQUENCE: 8
cttctaatgg agccccacct                                              20

<210> SEQ ID NO 9
<211> LENGTH: 21
<212> TYPE: DNA
<213> ORGANISM: Artificial Sequence
<220> FEATURE:
<223> OTHER INFORMATION: Wnt3 reverse primer

<400> SEQUENCE: 9
gaggccagag atgtgtactg c                                            21

<210> SEQ ID NO 10
<211> LENGTH: 20
<212> TYPE: DNA
<213> ORGANISM: Artificial Sequence
<220> FEATURE:
<223> OTHER INFORMATION: Axin2 forward primer

<400> SEQUENCE: 10
aacctatgcc cgtttcctct                                              20

<210> SEQ ID NO 11
<211> LENGTH: 20
<212> TYPE: DNA
<213> ORGANISM: Artificial Sequence
<220> FEATURE:
<223> OTHER INFORMATION: Axin2 reverse primer

<400> SEQUENCE: 11
gagtgtaaag acttggtcca                                              20

<210> SEQ ID NO 12
<211> LENGTH: 20
<212> TYPE: DNA
<213> ORGANISM: Artificial Sequence
<220> FEATURE:
<223> OTHER INFORMATION: Ctnnb1 forward primer

<400> SEQUENCE: 12
atggagccgg acagaaaagc                                              20

<210> SEQ ID NO 13
<211> LENGTH: 20
<212> TYPE: DNA
<213> ORGANISM: Artificial Sequence
<220> FEATURE:
<223> OTHER INFORMATION: Ctnnb1 reverse primer

<400> SEQUENCE: 13
tgggaggtgt caacatcttc                                              20

-continued

```
<210> SEQ ID NO 14
<211> LENGTH: 20
<212> TYPE: DNA
<213> ORGANISM: Artificial Sequence
<220> FEATURE:
<223> OTHER INFORMATION: Lgr5 forward primer

<400> SEQUENCE: 14
cctgtccagg ctttcagaag                                            20

<210> SEQ ID NO 15
<211> LENGTH: 20
<212> TYPE: DNA
<213> ORGANISM: Artificial Sequence
<220> FEATURE:
<223> OTHER INFORMATION: Lgr5 reverse primer

<400> SEQUENCE: 15
ctgtggagtc catcaaagca                                            20

<210> SEQ ID NO 16
<211> LENGTH: 25
<212> TYPE: DNA
<213> ORGANISM: Artificial Sequence
<220> FEATURE:
<223> OTHER INFORMATION: beta-actin forward primer

<400> SEQUENCE: 16
tggaatcctg tggcatccat gaaac                                      25

<210> SEQ ID NO 17
<211> LENGTH: 25
<212> TYPE: DNA
<213> ORGANISM: Artificial Sequence
<220> FEATURE:
<223> OTHER INFORMATION: beta-actin reverse primer

<400> SEQUENCE: 17
taaaacgcag ctcagtaaca gtccg                                      25

<210> SEQ ID NO 18
<211> LENGTH: 20
<212> TYPE: DNA
<213> ORGANISM: Artificial Sequence
<220> FEATURE:
<223> OTHER INFORMATION: pdh forward primer

<400> SEQUENCE: 18
aaccgattat tgaagcggca                                            20

<210> SEQ ID NO 19
<211> LENGTH: 20
<212> TYPE: DNA
<213> ORGANISM: Artificial Sequence
<220> FEATURE:
<223> OTHER INFORMATION: pdh reverse primer

<400> SEQUENCE: 19
atattggcgg cttcgtgaaa                                            20

<210> SEQ ID NO 20
<211> LENGTH: 20
<212> TYPE: DNA
<213> ORGANISM: Artificial Sequence
<220> FEATURE:
```

-continued

```
<223> OTHER INFORMATION: mmd forward primer

<400> SEQUENCE: 20
gaccaagaag gaacgcctca                                                    20

<210> SEQ ID NO 21
<211> LENGTH: 20
<212> TYPE: DNA
<213> ORGANISM: Artificial Sequence
<220> FEATURE:
<223> OTHER INFORMATION: mmd reverse primer

<400> SEQUENCE: 21
gttccgtcac cttgcattcg                                                    20

<210> SEQ ID NO 22
<211> LENGTH: 20
<212> TYPE: DNA
<213> ORGANISM: Artificial Sequence
<220> FEATURE:
<223> OTHER INFORMATION: Universal 16S rDNA forward primer

<400> SEQUENCE: 22
actcctacgg gaggcagcag                                                    20

<210> SEQ ID NO 23
<211> LENGTH: 17
<212> TYPE: DNA
<213> ORGANISM: Artificial Sequence
<220> FEATURE:
<223> OTHER INFORMATION: Universal 16S rDNA reverse primer

<400> SEQUENCE: 23
attaccgcgg ctgctgg                                                       17

<210> SEQ ID NO 24
<211> LENGTH: 20
<212> TYPE: DNA
<213> ORGANISM: Artificial Sequence
<220> FEATURE:
<223> OTHER INFORMATION: A. muciniphila 16S rDNA forward primer

<400> SEQUENCE: 24
cagcacgtga aggtggggac                                                    20

<210> SEQ ID NO 25
<211> LENGTH: 20
<212> TYPE: DNA
<213> ORGANISM: Artificial Sequence
<220> FEATURE:
<223> OTHER INFORMATION: A. muciniphila 16S rDNA reverse primer

<400> SEQUENCE: 25
ccttgcggtt ggcttcagat                                                    20
```